United States Patent [19]
Hansen et al.

[11] Patent Number: 5,486,271
[45] Date of Patent: Jan. 23, 1996

[54] PROCESS FOR PREPARING PERFLUOROALKANESULFONYL FLUORIDES

[75] Inventors: John C. Hansen, Lakeland; Herward A. Vogel, St. Paul, both of Minn.

[73] Assignee: Minnesota Mining and Manufacturing Company, Saint Paul, Minn.

[21] Appl. No.: 320,527

[22] Filed: Oct. 11, 1994

[51] Int. Cl.$^6$ .............................. C25B 3/00; C25B 3/08
[52] U.S. Cl. ............................................ 204/59 F; 204/81
[58] Field of Search ..................... 204/59 R, 59 F, 204/81

[56] References Cited

U.S. PATENT DOCUMENTS

| | | | |
|---|---|---|---|
| 2,519,983 | 8/1950 | Simons | 204/62 |
| 2,732,398 | 1/1956 | Brice et al. | 260/503 |
| 3,028,321 | 4/1962 | Danielson et al. | 204/59 |
| 3,333,007 | 7/1967 | Scanley | 260/607 |
| 3,419,595 | 12/1968 | Hansen | 260/456 |
| 3,692,643 | 9/1972 | Holland | 204/59 R |
| 4,411,841 | 10/1983 | Geisler | 260/543 F |
| 4,739,103 | 4/1988 | Hansen et al. | 560/125 |
| 4,970,337 | 11/1990 | Bielefeldt et al. | 562/829 |
| 5,326,437 | 7/1994 | Bulan et al. | 204/59 R |

FOREIGN PATENT DOCUMENTS

| | | |
|---|---|---|
| 582192 | 2/1994 | European Pat. Off. . |
| 2-99586 | 12/1991 | Japan . |

OTHER PUBLICATIONS

Ser. No. 08/085,540 filed Jun. 30, 1993 to Behr.
Willis, C. J., "Inorganic Analogues of Olefins" Thesis Cambridge University, pp. 32–43, 110–111 Sep. (1958).
March, J., *Advanced Organic Chemistry*, Third Edition, John Wiley & Sons, New York, pp. 358, 363, 376, 411, 445, and 1089 No Month (1985).
Farng and Kice, "Substituted Reactions of Alkanesulfonyl Derivitives," *J. Am. Chem. Soc.* No Month 1981, 103, 1137–1145.
*Fluorine Chemistry*, edited by J. H. Simons, pub. No Month 1950 Academic Press, Inc., New York, vol. 1, pp. 416–418.
Gard et al., "New Perfluoro and Perfluoralkoxy Sulfonyl Fluorides Part V. Fluorination Studies," *Journal of Fluorine Chemistry*, 55, pp. 313–321, (1991) No Month.
Stang, P. J. and White, M. J., "Trific Acid and It's Derivatives," *Aldrichima Acta*, vol. 16, pp. 15–22 (1983) No Month.
Novikova et al., "Synthesis of trifluoromethyl sulfonic acid fluoride by direct gas–phase fluorination of (fluorosulphonyl) difuoroacetic acid fluoride," *Journal of Fluorine Chemistry*, vol. 58, Nos. 2–3, Aug.–Sep. 1992, p. 326.
Rozhkov, I. N., "Anodic Fluorination," *Organic Electrochemistry*, Second Edition, Marcel Dekker, Inc., New York and Basel, pp. 803–825 (1983) No Month.
*Preparation, Properties, and Industrial Applications of Organofluorine Compounds*, Banks, ed., John Wiley & Sons, New York, pp. 37–43, (1982) No Month.
Howells et al., "Trifluoromethanesulfonic Acid and Derivatives," *Chemical Reviews*, vol. 77, Feb. 1977, pp. 69–92.
Hollitzer et al., "The Electrochemical Perfluorination (ECPF) Of Propanesulfonyl Fluorides, Part I. Preparation and ECPF Of 1–Propanesulfonyl Fluoride and 1,3–Propanedisulfonyl Difloride," *Journal of Fluorine Chemistry*, 35, pp. 329–341, (1991) No Month.
Volkov, N. D., et al., "Preparation of Halodifluoromethanesulfonic Acid Derivatives," *Synthesis*, pp. 972–975 (1979) No Month.
Clark, "Perfluoroalkyl Derivatives of the Elements," *Advances in Fluorine Chemistry*, vol. 3, pp. 19, 25–29, 55–56, Butterworths, London (1963) No Month.
Sokol'skii, G. A. and Dmitriev, M. A., "Electrochemical Fluorination of Methyl Chlorosulfonate," *Zhurnal Obshchei Khimii*, vol. 31, No. 3, pp. 706–710, (Mar. 1961).
Sokol'skii, G. A. and Dmitriev, M. A. "Hexafluorodimethylsulfonate," *Zhurnal Obshchei Khimii*, vol. 31, No. 4, pp. 1107–1110, (Apr. 1961).
Haszeldine, R. J. and Kidd, J. M., "Perfluoroalkyl Derivatives of Sulphur . . . ," *J. of the Chemical Society*, pp. 2901–2910 May (1955).

*Primary Examiner*—John Niebling
*Assistant Examiner*—Edna Wong
*Attorney, Agent, or Firm*—Douglas B. Little; Gary L. Griswold; Walter N. Kirn

[57] ABSTRACT

A process for preparing perfluoroalkanesulfonyl fluorides, e.g., perfluoromethanesulfonyl fluoride, is described which comprises electrochemically fluorinating in the presence of anhydrous hydrogen fluoride mono-, di- or tri- alkylsulfonyl alkyl esters or amides, or mono-, bis- or tris- alkylsulfonyl alkanes or disulfones. The process can be used to prepare perfluoroalkanesulfonyl fluorides in good yield and can be both more electrically-efficient and more fluorine-efficient than the conventional preparative method involving the electrochemical fluorination of hydrocarbon alkanesulfonyl halides.

20 Claims, No Drawings

PROCESS FOR PREPARING PERFLUOROALKANESULFONYL FLUORIDES

FIELD OF THE INVENTION

This invention relates to a process for preparing perfluoroalkanesulfonyl fluorides by electrochemical fluorination.

BACKGROUND OF THE INVENTION

Perfluoroalkanesulfonyl fluorides are useful as starting materials for the preparation of a variety of useful compounds. For example, perfluoromethanesulfonyl fluoride can be used to prepare perfluoromethanesulfonic acid, which has been reported to be the strongest of all known monoprotic organic acids. (See R. D. Howells and J. D. McCown, Chem. Rev., 77, 69 (1977).) Perfluoroalkanesulfonyl fluorides can also be utilized to prepare perfluoroalkanesulfonamides (which are useful as herbicides, antimicrobials, and pharmaceuticals) and salts such as lithium perfluoroalkanesulfonates and lithium bis (perfluoroalkanesulfonyl)imides (which are useful as electrolyte salts for battery applications). (See P. J. Stang and M. R. White, Aldrichimica Acta, 16, 15 (1983) and Kirk-Othmer *Encyclopedia of Chemical Technology*, Fourth Edition, Volume 3, page 1017, John Wiley & Sons, New York, (1992).)

Perfluoroalkanesulfonyl fluorides have been prepared from a variety of different starting materials by such methods as electrochemical fluorination, direct fluorination, and photolysis.

For example, U.S. Pat. No. 2,732,398 (Brice et al.) discloses the preparation of perfluoroalkanesulfonyl fluorides by the electrochemical fluorination (ECF) in anhydrous liquid hydrogen fluoride of the corresponding hydrocarbon alkanesulfonyl halides.

J. Fluorine Chem. 58, 326 (1992) (M. Novikova et al.) describes the preparation of perfluoromethanesulfonyl fluoride by direct gas-phase fluorination of (fluorosulfonyl)difluoroacetyl fluoride.

Syntheses, 972 (1979) (N. D. Volkov et al.) discloses the preparation of halodifluoromethanesulfonyl fluorides by photolysis of the corresponding 2-halo-2-oxodifluoroethanesulfonyl fluorides.

SUMMARY OF THE INVENTION

Accordingly, this invention provides a process for preparing perfluoroalkanesulfonyl fluorides comprising electrochemically fluorinating in the presence of anhydrous hydrogen fluoride a compound of the Formula I $$(RSO_2)_n X \qquad \qquad I$$

wherein R is alkyl of 1 to 20 carbon atoms in which the carbon chain may be interrupted by one or more ether oxygen atoms;

(a) n is 1, and X is —$R^i$, —$OR^i$, —$NR^{ii}R^{iii}$ or —$SO_2R$, in which R is as defined above; $R^i$ is R; $R^{ii}$ and $R^{iii}$ are each independently hydrogen or alkyl of 1 to 8 carbon atoms in which the carbon chain may be interrupted by one or more ether oxygen atoms, or when taken together with the nitrogen atom form a five to seven membered heterocyclic ring optionally interrupted by a heteroatom selected from nitrogen, oxygen and sulfur; with the proviso of excluding dimethylsulfone and diethylsulfone;

(b) n is 2, and X is —$R^i$—, —$OR^i$—, —$OR^{iv}O$— or

in which $R^i$ is R or alkylene of 1 to 8 carbon atoms optionally containing one or more ether oxygen atoms as defined above; $R^{iv}$ is alkylene of 1 to 8 carbon atoms; $R^{ii}$ is hydrogen or alkyl of 1 to 8 carbon atoms in which the carbon chain may be interrupted by one or more ether oxygen atoms, or (c) n is 3, and X is

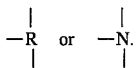

A preferred aspect of this invention is using a compound of the formula $(CH_3SO_2)_n X$ for preparing perfluoromethane sulfonyl fluorides. Most preferably, dimethyl disulfone is utilized.

The process of the invention provides a route to perfluoroalkanesulfonyl fluorides which can be both more electrically-efficient and more fluorine-efficient than the conventional route involving the electrochemical fluorination of hydrocarbon alkanesulfonyl halides. The compounds of Formula I possess significant advantages as feed materials in the electrochemical fluorination process over the hydrocarbon alkane sulfonyl halides, e.g. methane sulfonyl fluoride, and dimethyl sulfone. Methane sulfonyl fluoride is highly toxic and dimethyl sulfone generates, besides perfluoromethanesulfonyl fluoride (PMSF), large amounts of low boiling $CF_4$ gas which is a difficult to recover, low commercial value by-product. Dimethylsulfone and its solution in anhydrous HF create severe metal corrosion. As a high melting point solid, dimethylsulfone presents handling problems in the feed process.

The compounds of Formula I, e.g. alkyl methane sulfonates, are easier to handle in the electrochemical fluorination and generate perfluoromethanesulfonyl fluoride and a perfluoroalkane (and carboxylic acid fluorides when the raw material is a sulfonate ester) as a co-product. The co-products are often more readily recovered and have good commercial value. For example in the electrochemical fluorination of octyl methanesulfonate, perfluoromethanesulfonyl fluoride and perfluorooctane are recovered. The latter is also a valuable product used, for example, as a thermal transfer media, solvent, refrigerant, etc.

Another advantage of using the compounds of Formula I in the electrochemical fluorination process of the present invention is the fact that carbon-sulfur bond cleavage (which would provide a highly toxic, undesirable product, $SO_2F_2$) does not predominate.

The process of the invention provides perfluoroalkanesulfonyl fluorides in good yield by the electrochemical fluorination of the compounds of Formula I which are commercially available or can be prepared from readily available industrial starting materials. Thus raw materials are not wasted making by-products of little value. In addition, electricity is better utilized because of the good yields.

DETAILED DESCRIPTION OF THE INVENTION

The compounds of the present invention utilized in the electrochemical fluorination process are those of Formula I defined above.

The term "alkyl" is followed by the designated numbers of carbon atoms in a hydrocarbon chain and includes a straight or branched aliphatic hydrocarbon radical within the numbered range, e.g. methyl, ethyl, propyl, isopropyl, butyl, sec-butyl, isobutyl, tert-butyl, hexyl, octyl, decyl, dodecyl, and the like.

The term "alkylene" is a hydrocarbon radical of the formula —$(CH_2)_n$— where n may vary from 1 to 8 unless designated otherwise and includes, for example, methylene, ethylene, propylene, butylene, and the like.

The term "five to seven membered heterocyclic ring optionally interrupted by a heteroatom selected from nitrogen, oxygen and sulfur" includes, for example, pyrrolidine, piperidine, homopiperidine, piperazine, morpholine, thiomorpholine, and the like.

A preferred embodiment of compounds of Formula I defined above and utilized in the process of the invention is a compound wherein R is alkyl of 1 to 8 carbon atoms in which the carbon chain may be interrupted by one or more ether oxygen atoms.

A more preferred embodiment of Formula I is a compound wherein n is 1; X is as defined above, except $R^i$ is R in which R is alkyl of 1 to 8 carbon atoms in which the carbon chain may be interrupted by one or more ether oxygen atoms, and $R^{ii}$ and $R^{iii}$ are each independently hydrogen or alkyl of 1 to 4 carbon atoms or when taken together with the nitrogen atom form a 5- or 6- membered heterocyclic ring optionally interrupted by a heteroatom selected from nitrogen, oxygen and sulfur.

Another more preferred embodiment of Formula I is a compound wherein n is 2; X is as defined above; $R^i$ is R, in which R is alkyl of 1 to 8 carbon atoms in which the carbon chain may be interrupted by one or more ether oxygen atoms, or alkylene of 1 to 8, more preferably 1 to 4 carbon atoms optionally containing an ether oxygen atom, and $R^{ii}$ is hydrogen or alkyl of 1 to 8, more preferably 1 to 4 carbon atoms.

When one of the desired products in the electrochemical fluorination process is perfluoromethanesulfonyl fluoride, the precursor compound utilized is of the Formula II $$(CH_3SO_2)_nX \qquad II$$

wherein n is 1, and X is —$R^i$, —$OR^i$, —$NR^{ii}R^{iii}$ or —$SO_2R$, in which R is alkyl of 1 to 20 carbon atoms in which the carbon chain may be interrupted by one or more ether oxygen atoms; $R^i$ is alkyl of 2 to 20 carbon atoms in which the carbon chain may be interrupted by one or more ether oxygen atoms; $R^{ii}$ and $R^{iii}$ are each independently hydrogen or alkyl of 1 to 8 carbon atoms in which the carbon chain may be interrupted by one or more ether oxygen atoms, or when taken together with the nitrogen atom form a five to seven membered heterocyclic ring optionally interrupted by a heteroatom selected from nitrogen, oxygen and sulfur;

n is 2, and X is —$R^i$—, —$OR^i$—, —$OR^{iv}O$— or

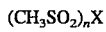
—$NR^{ii}$, in which $R^i$ is R or alkylene of 1 to 8 carbon atoms optionally containing one or more ether oxygen atoms; $R^{iv}$ is alkylene of 1 to 8 carbon atoms; and $R^{ii}$ is hydrogen or alkyl of 1 to 8 carbon atoms in which the carbon chain may be interrupted by one or more ether oxygen atoms, or n is 3, and X is

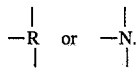

A preferred embodiment of a compound of Formula II utilized in the process of the invention is a compound wherein n is 1; X is as defined above, in which R is alkyl of 1–8 carbon atoms; $R^i$ is alkyl of 2 to 8 carbon atoms optionally containing an ether oxygen atom, and $R^{ii}$ and $R^{iii}$ are each independently hydrogen or alkyl of 1 to 4 carbon atoms or when taken together with the nitrogen atom form a 5- or 6-membered heterocyclic ring optionally interrupted by a heteroatom selected from nitrogen, oxygen and sulfur.

Another preferred embodiment of Formula II is a compound wherein n is 2; X is as defined above; $R^i$ is R, in which R is alkyl of 1–8 carbon atoms, or alkylene of 1 to 4 carbon atoms optionally containing an ether oxygen atom; $R^{iv}$ is alkylene of 1 to 4 carbon atoms; and $R^{ii}$ is hydrogen or alkyl of 1 to 4 carbon atoms.

Particularly valuable precursor compounds utilized in the process of this invention include:
isobutyl methanesulfonate,
octyl methanesulfonate,
isopropyl methanesulfonate,
butyl methanesulfonate,
methyl methanesulfonate,
methyl butyl sulfone
methyl octyl sulfone
methane sulfonamide,
morpholino-methane sulfonamide,
tris(methyl sulfonyl) methane,
ethylene glycol dimethylsulfonate,
1,1 bis(methyl sulfonyl) butane,
hexyl octyl sulfone,
bis(6-hexyl sulfonyl) methane,
bis(8-octyl sulfonyl) methane,
methyl ethanesulfonate,
ethyl ethanesulfonate,
ethyl methanesulfonate,
bis(methyl sulfonyl) methane,
N, N-bis-methane sulfonimide, and
dimethyl disulfone.

Compounds of Formulas I and II are either commercially available or can be prepared by known methods from commercially available starting materials. Thus, for example, sulfonate esters can be prepared by the reaction of an alcohol with a sulfonic acid or sulfonyl halide as described in March, *Advanced Organic Chemistry*, John Wiley & Sons, New York, 1985, p. 358.

Sulfonamides may be prepared by N-alkylation of sulfonamides (March, ibid., p. 376 or p. 411), or by the reaction of an amine with a sulfonic acid, ester or sulfonyl halide (March, ibid., p. 445).

Sulfones may be prepared by the reaction of an alkyl halide with a sulfinate (March ibid., p. 363) or by the oxidation of sulfides or sulfoxides (March ibid., p. 1089).

Disulfones may be prepared by the procedure described by Farng and Kice in *J. Am. Chem. Soc.*, 1981, 103, 1137–1145.

The electrochemical fluorination of the above-described precursor compounds can be carried out by introducing, e.g., by pumping, at least one precursor compound of Formula I and/or Formula II to a Simons electrochemical fluorination cell containing anhydrous hydrogen fluoride (or to which anhydrous hydrogen fluoride is simultaneously or subsequently added). The Simons electrochemical fluorination cell is an electrolytic cell in which is suspended an electrode pack comprising a series of alternating and closely-spaced cathode plates (typically made of iron or nickel or nickel alloy) and anode plates (typically made of nickel). The electrodes are connected in parallel through electrode posts. The cell body can be made of, for example, carbon steel, which may have a coating of corrosion resistant material, and is usually provided with a cooling jacket, a valved outlet pipe at the bottom through which can be drained the settled liquid cell product ("drainings"), a valved inlet pipe at the top of the cell for charging the cell with the precursor compound(s) and liquid anhydrous hydrogen fluoride, and an outlet pipe at the top of the cell for removing gaseous cell products evolved in operation of the cell.

The gaseous stream leaving the cell can comprise HF, hydrogen, $OF_2$ (oxygen difluoride) and other gases. The outlet pipe can be connected to a refrigerated condenser for condensing hydrogen fluoride vapors and relatively hydrogen fluoride-insoluble fluorochemical products. The resulting condensed materials can be phase-separated, the fluorochemical products collected, and the hydrogen fluoride returned to the cell. The gaseous stream from the top of the cell may pass through a packed bed of catalyst (e.g. silver or silver fluoride or aluminum support) in which HF is removed. U.S. Pat. No. 2,519,983 contains a drawing of such a Simons electrolytic cell and its appurtenances, and a description and photographs of laboratory and pilot plant cells appear at pages 416–18 of Volume I of *Fluorine Chemistry*, edited by J. H. Simons, published in 1950 by Academic Press, Inc., New York.

The Simons (ECF) cell can be operated at average applied direct current cell voltages in the range of from about 4 to about 8 volts (sufficiently high, but not so high as to generate free fluorine), at current densities of from about 10 to about 600 amps/m² of active anode surface, preferably 20 to 300 amps/m², at substantially atmospheric or ambient pressure or higher, e.g. 207 KiloPascals (KPa), and at temperature ranging from below about 0° C. to about 20° C. or as high as about 60° C. (so long as the electrolytic solution remains liquid.) The cell is run at boiling condition for the cell liquid but a liquid phase is maintained. Temperature can be controlled by controlling back pressure in the cell itself, by means of a back pressure control valve on the gas outlet line. The initial amount of precursor compound(s) in the anhydrous hydrogen fluoride can be, for example, from about 5 to about 20 weight percent, and both the precursor compound(s) and the anhydrous hydrogen fluoride can be replenished from time to time.

If desired, a conventional conductivity additive, such as dimethyldisulfide (DMDS), lithium fluoride, methyl acetate, sodium fluoride, acetic anhydride, or an organic sulfur-containing compound such as that described in U.S. Pat. Nos. 3,028,321 (Danielson), 3,692,643 (Holland), and 4,739,103 (Hansen), can be added to the cell to increase the conductivity of the cell contents. The amount of said additive can be, for example, from about 1 to 20 percent by weight (based upon the weight of the precursor compound(s)). In making higher molecular weight fluoroalkanes, DMDS appears to be beneficial.

In the experiments made in developing this invention, gaseous ECF reaction products were collected using condensers at –40° C. and decanter vessels. In collecting PMSF, collection traps cooled with dry ice (solid $CO_2$ at –78° C.) and some with liquid nitrogen (–196° C.) were used. HF concentration was typically in the range of 70 to 99 weight percent in the ECF cell.

Other details of the Simons electrochemical fluorination process and cell will be omitted here in the interest of brevity, and the disclosures of such technology in the above-cited references to such technology can be referred to for such detail, which disclosures are incorporated herein by reference. ECF production scale cells vary in size from small cells operating at currents of from less than 100 amps to large cells which use 10,000 amps or more.

The process of the invention can be carried out continuously (continuously introducing precursor compound(s) to the cell and continuously withdrawing liquid cell product), semi-continuously or batchwise. The term semi-continuously can mean: continuously introducing precursor until the total charge is complete, and then reacting to the desired extent; or intermittently introducing precursor in a number of aliquots. The continuous mode of operation is preferred for large-scale operation, as it enables better control of the operating variables. The level of liquid in the cell is preferably controlled, and both HF and $(RSO_2)_nX$ can be replenished during the reaction.

The desired perfluoroalkanesulfonyl fluoride product is preferably recovered, for example, by condensation followed by phase-separation into an upper hydrogen fluoride-containing phase and a lower fluorochemical-containing phase (e.g., by use of a decanter) and subsequent draining of the lower phase. The drainings can be further purified, if desired, by passage through a column containing sodium fluoride in order to remove any residual hydrogen fluoride. In addition, low temperature distillation can be used to isolate the desired fluorochemical products.

The perfluoroalkanesulfonyl fluoride products of the process are useful as starting materials for the preparation of a variety of compounds having utility, for example, as strong acids, herbicides, pesticides, antimicrobials, pharmaceuticals, and as electrolyte salts for battery or fuel cell applications.

This invention is further illustrated by the following examples, but the particular materials and amounts thereof recited in these examples, as well as other conditions and details, should not be construed to limit this invention.

EXAMPLES

EXAMPLE 1

Electrochemical fluorination of METHYL METHANESULFONATE

An electrochemical fluorination cell of the type described in U.S. Pat. No. 2,519,983 (Simons) was fitted, in series, with a –40° C. condenser, a –78° C. condenser, and liquid nitrogen condenser. The cell was charged with anhydrous HF and 615 g of methyl methane sulfonate was fed by a pump in a semi-continuous manner over a period of 166 hours (average of 0.305 g/1.0 ampere-hour of current passed), while electrolyzing the resulting solution using an average voltage of 6.5 volts at an average current of 12.2 amps at 55° C. and at a pressure of 0.21 MPa (30 psig). The gaseous products from the cell were passed to the –40° C. condenser where most of the HF condensed and was returned to the cell. The fluorochemical products produced were collected in the –78° C. condenser and the liquid nitrogen condenser. The collected product stream was analyzed using gas chromatography and Fourier transform infrared spectroscopy to determine product structures and yields.

Perfluoromethanesulfonyl fluoride ($CF_3SO_2F$) was collected from the latter two condensers at an average rate of 15.5 g/50 ampere-hour (65% of theoretical yield based on current flow (theo.)). $COF_2$ was also collected, but the rate was not determined.

EXAMPLE 2

Electrochemical fluorination of OCTYL METHANESULFONATE

Octyl methanesulfonate was electrochemically fluorinated as in Example 1 with the addition of dimethyl disulfide as a conductivity additive (10 wt % of the octyl methanesulfonate) at an average of 6.7 volts, an average 14.5 amps, an average of 52° C. and 0.21 MPa (30 psig) control. $CF_3SO_2F$ was produced at a rate of about 0.042 g/1.0 ampere-hour of current passed (35% theo.), based upon cleavage of the sulfur-oxygen bond. The other major product formed was $C_8F_{18}$.

EXAMPLE 3

Electrochemical fluorination of ISOPROPYL METHANESULFONATE

Isopropylmethane sulfonate was electrochemically fluorinated as in Example 1 at 6.7 volts average, at 13.5 amps average current, 45°–55° C. and 0.17–0.21 MPa (25 to 30 psig) control. Perfluoromethanesulfonyl fluoride was produced at 0.12 g to 0.15 g/1.0AH. (50% to 60% theo). $C_3F_8$ was also produced at 0.13 g to 0.18 g/1.0 AH or about 43% to 60% theo. A minor amount of unidentified fluorocarbons with boiling points above 60° C. was also produced.

EXAMPLE 4

Electrochemical fluorination of BUTYL METHANESULFONATE

Electrochemical fluorination as in Example 1 was carried out with the addition of dimethyl disulfide as a conductivity additive (10 wt % of the octyl methanesulfonate) at about the same temperatures and pressures, averaging 25 amps/ft.$^2$ (269a/m$^2$) current at 6.1 average volts and producing perfluoromethanesulfonyl fluoride at 60% theo. or about 0.18 g/1.0 ampere-hour. The other major cleavage product was $C_4F_{10}$, also made at 0.18 g/1.0 ampere-hour (39% theo.). A minor amount of unidentified fluorocarbons with boiling points above that of $C_4F_{10}$ was also produced.

EXAMPLE 5

Electrochemical fluorination of METHYL BUTYL SULFONE

This was electrochemically fluorinated as in Example 1 at 5.6 volts average, 13.8 amps average current, 0.14 MPa (20 psig) control and about 45° C. Perfluoromethanesulfonyl fluoride was produced at about 20% theo. (0.041 g/1.9 ampere-hour) and $C_4F_{10}$ at about 25% theo. (0.13 g/1.0 ampere-hour). In addition $C_4F_9SO_2F$ was produced at about 7–8% theo. (0.0314 g/1.0 ampere-hour) and perfluoromethyl-butyl sulfone ($CF_3SO_2C_4F_9$) was produced at about 10% theo. (0.033 g/1 ampere-hour).

EXAMPLE 6

Electrochemical fluorination of METHYL OCTYL SULFONE

This was electrochemically fluorinated as in Example 1 at 6.3 volts average, 10.8 amps average current, an average of 0.10 MPa (15 psig) control and an average of about 40° C. Perfluoromethanesulfonyl fluoride was produced at 40% theo. or 0.054 g/ampere-hour. Perfluoroctane sulfonyl fluoride was produced at 5% theo. or 0.0226 g/ampere-hour. Perfluorooctane was produced at 41% theo. or 0.16 g/ampere-hour.

EXAMPLE 7

Electrochemical fluorination of METHANE SULFONAMIDE 450 g. Methane sulfonamide was dissolved in anhydrous HF and fed (at an average rate of 0.143 g/1.0 (AH) ampere-hour)) to a 750 c.c. volume electrochemical cell operating at an average of 16 amps at 5.5 volts, atmospheric pressure and about 20° C.

The methane sulfonamide was fed by means of a gravity charger, an apparatus for conveying liquids to a vessel at very small flow rates. A gravity charger comprises essentially: a reservoir of the raw material to be conveyed (methane sulfonamide in this case); a tube connecting the reservoir to the ECF cell; a pressure equalizing tube connecting the tops of the ECF cell and the reservoir; and a lifting means capable of raising the reservoir slowly to change the static head pressure difference between the raw material in the reservoir and the liquid in the ECF cell. In this case, the lifting means was an electric motor which drove a threaded rod (the rotational speed of which was adjustable), which, in turn, slowly advanced a mechanical means connected to the reservoir. As the reservoir lifted, the slow increase in static head caused the liquid raw material to flow into the ECF cell.

Perfluoromethanesulfonyl fluoride was produced at about 80% theo. or 0.38 g/ampere-hour, with some minor cleavage to $CF_4$, $SO_2F_2$ and $SOF_4$ with the nitrogen lost as $NF_3$.

EXAMPLE 8

Electrochemical fluorination of MORPHOLINOMETHANESULFONAMIDE

Morpholino methanesulfonamide was electrochemically fluorinated under the same operating conditions as Example 7 at 5.2 volts average and 12.1 amps average current. Perfluoromethanesulfonyl fluoride was produced at about 70% theo. or about 0.116 g/ampere-hour at a feed rate of about 0.155 g/ampere-hour. Perfluoromorpholine was also made at about 77% theo.

EXAMPLE 9

Electrochemical fluorination of DIMETHYL DISULFONE 11.8 g Dimethyl disulfone was dissolved in anhydrous HF and then fed (in three approximately equal aliquots by means of a syringe system) into a small (about 180 cc. volume) cell semi-continuously. The cell was run at 6.2 volts average, 2 amps average current, atmospheric pressure and about 20° C. The production rates of perfluoromethanesulfonyl fluoride varied between 73% theo. and 88% theo. or 0.60 g/ampere-hour to 0.72 g/ampere-hour of current passed. There were minor amounts of the cleavage products $CF_4$, $CF_3H$. $SO_2F_2$ and $SOF_4$.

EXAMPLE 10

Electrochemical fluorination of ETHYLENE GLYCOL DIMETHANESULFONATE $CH_3SO_3CH_2CH_2O_3SCH_3$ was fluorinated as in Example 1 at an average of 20 amps, an average 7.0 volts, 0.1 MPa (15 psig) control and 40° C. Perfluoromethanesulfonyl fluoride rates were about 15% theo. or 0.078 g/ampere-hour. In addition to the desired perfluoromethanesulfonyl fluoride, other cleavage products including $COF_2$, $SO_2F_2$, $CF_4$, $CO_2$, $CF_3H$ and $SOF_4$ were produced.

EXAMPLE 11

Electrochemical fluorination of BIS(METHYLSULFONYL)METHANE

This was fluorinated as in Example 1 at an average of 20 amps, an average of 5.4 volts, 0.17MPa (25 psig) control and 50° C. Perfluoromethanesulfonyl fluoride was produced at about 40 to 50% theo. 0.228 g/ampere-hour to 0.286 g/ampere-hour. No perfluorinated product corresponding to the starting material was evident in the product.

EXAMPLE 12

Electrochemical fluorination of 1,1 BIS(METHYL SULFONYL BUTANE)

This was fluorinated as in Example 1 at an average of 11 amps, an average of 5.7 volts, 0.034 to 0.068 MPa (5 to 10 psig), and 25° C. to 30° C. Perfluoromethanesulfonyl fluoride was produced at 62% theo. or 0.22 g/ampere-hour. The other desired material $C_4F_{10}$ was made at about 48% theo. or 0.136 g/ampere-hour.

EXAMPLE 13

Electrochemical fluorination of BIS(6-HEXYL SULFONYL)METHANE

This was electrochemically fluorinated as in Example 1 with the addition of dimethyl disulfide as a conductivity additive (5 wt % of the feed material). The solid feed material was dissolved in HF and fed to the electrochemical fluorination cell in a semi-continuous manner over a period of 81.5 hours, while running at an average of 20 amps, an average voltage of 6.3, at 0.21 MPa (30 psig) control and an average temperature of 55° C. Cleavage of the molecule was the predominant reaction with $C_6F_{14}$ being the major product formed at about 40% theo. with $C_6F_{13}SO_2F$ formed at about 20% theo. and perfluoromethanesulfonyl fluoride formed at 10% of theo. Small amounts of the perfluoromethyl-hexyl sulfone were also found.

EXAMPLE 14

Electrochemical fluorination of BIS(8-OCTYL SULFONYL) METHANE

This was electrochemically fluorinated as in Example 1 with the addition of dimethyl disulfide as a conductivity additive (5 wt % of the feed material). The cell was operated at an average of 20 amps, an average of 6.5 volts, 0.21 MPa (30 psig) control and an average temperature of 55° C. Yields of perfluoromethanesulfonyl fluoride were about 5% to 10% theo. with $C_8F_{17}SO_2F$ produced at <10% theo. and $C_8F_{10}$ being the major product formed during the 84.4 hour run.

EXAMPLE 15

Electrochemical fluorination of ETHYL METHANESULFONATE

This was electrochemically fluorinated as in Example 1 with the addition of LiF as a conductivity additive (+¼ wt % of the feed material). The cell was operated at an average of 30 amps, at an average of 7.5 volts, 0.17 MPa (25 psig) control and about 50° C. Perfluoromethanesulfonyl fluoride was produced and collected at about 58% theo average 0.218 g/1.0 ampere-hour and $COF_2$, $C_2F_6$ $SO_2F_2$, $SOF_4$, $CF_3H$ and $CF_4$, were other cleavage products from this feed. Neither $OF_2$ nor perfluoroethylmethane sulfonate were found in the collected products.

EXAMPLE 16

Electrochemical fluorination of HEXYL-OCTYL SULFONE

This was electrochemically fluorinated as in Example 1 with the addition of dimethyl disulfide as a conductivity additive (5 wt % of the feed material). The feed material was dissolved in anhydrous HF and fed to the cell semi-continuously. The cell was operated at an average of 21 amps, an average voltage of 6.0, an average of 0.17 MPa (25 psig) and about 50° C. over a period of 76 hours. During this short run the yields of $C_8F_{17}SO_2F$ were about 10% theo., as were the yields of $C_6F_{13}SO_2F$. The yields of the perfluoroalkanes predominated at about 25% theo. for both $C_6F_{14}$ and $C_8F_{18}$.

EXAMPLE 17

Electrochemical fluorination of ETHYL ETHANESULFONATE

This was electrochemically fluorinated as in Example 1 with the addition of LiF as a conductivity additive (¼ wt % of the feed material). The ECF cell was operated at an average of 28.5 amps, 6.3 volts average, and 0.21MPa (30 psig) control and about 55° C. Perfluoroethane sulfonyl fluoride was produced at about 10% theo. and perfluoromethanesulfonyl fluoride was produced at <5% theo. The major byproduct was $C_2F_6$ plus $SO_2F_2$ and $COF_2$.

What is claimed is:

1. A process of preparing perfluoroalkanesulfonyl fluorides comprising electrochemically fluorinating in the presence of anhydrous hydrogen fluoride a compound of the formula $(RSO_2)_nX$ wherein R is alkyl of 1 to 20 carbon atoms in which the carbon chain may be interrupted by one or more ether oxygen atoms;

(a) n is 1, and X is —$R^i$, —$OR^i$, —$NR^{ii}R^{iii}$ or —$SO_2R$, in which R is as defined above; $R^i$ is R; $R^{ii}$ and $R^{iii}$ are each independently hydrogen or alkyl of 1 to 8 carbon atoms in which the carbon chain may be interrupted by one or more ether oxygen atoms, or when taken together with the nitrogen atom form a five to seven membered heterocyclic ring optionally interrupted by a heteroatom selected from nitrogen, oxygen and sulfur; with the proviso of excluding dimethylsulfone and diethylsulfone;

(b) n is 2, and X is —$R^i$—, —$OR^i$—, —$OR^{iv}$O— or

—$NR^{ii}$, in which $R^i$ is an alkylene of 1 to 20 carbon atoms optionally containing one or more ether oxygen atoms; $R^{iv}$ is alkylene of 1 to 8 carbon atoms; $R^{ii}$ is hydrogen or alkyl of 1 to 8 carbon atoms in which the carbon chain may be interrupted by one or more ether oxygen atoms, or (c) n is 3, and X is

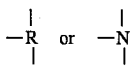

in which R is as defined above but with 3 bond sites, with the proviso that the electrochemical fluorination is conducted under the following conditions: current density of about 10 to 600 amps per square meter of anode surface; and a temperature sufficient to maintain a boiling hydrogen fluoride liquid phase during the fluorination.

2. The process of claim 1, wherein R is alkyl of 1–8 carbon atoms in which the carbon chain may be interrupted by one or more ether oxygen atoms.

3. The process of claim 2, wherein n is 1; $R^i$ is R, and $R^{ii}$ and $R^{iii}$ are each independently hydrogen or alkyl of 1 to 4 carbon atoms or when taken together with the nitrogen atom form a 5- or 6- membered heterocyclic ring optionally interrupted by a heteroatom selected from nitrogen, oxygen and sulfur.

4. The process of claim 2, wherein n is 2; $R^i$ is an alkylene group of 1 to 4 carbon atoms optionally containing an ether oxygen atom, and $R^{ii}$ is hydrogen or alkyl of 1 to 4 carbon atoms.

5. A process of preparing perfluoromethanesulfonyl fluoride comprising electrochemical fluorination in the presence of anhydrous hydrogen fluoride of a compound of the formula $(CH_3SO_2)_nX$ wherein (a) n is 1, and X is —$R^i$, —$OR^i$, —$NR^{ii}R^{iii}$ or —$SO_2R$, in which R is alkyl of 1 to 20 carbon atoms in which the carbon chain may be interrupted by one or more ether oxygen atoms; $R^i$ is alkyl of 2 to 20 carbon atoms in which the carbon chain may be interrupted by one or more ether oxygen atoms; $R^{ii}$ and $R^{iii}$ are each independently hydrogen or alkyl of 1 to 8 carbon atoms in which the carbon chain may be interrupted by one or more ether oxygen atoms, or when taken together with the nitrogen atom form a five to seven membered heterocyclic ring optionally interrupted by a heteroatom selected from nitrogen, oxygen and sulfur;

(b) n is 2, and X is —$R^i$—, —$OR^i$—, —$OR^{iv}$O— or

—$NR^{ii}$, in which $R^i$ is an alkylene of 1 to 20 carbon atoms optionally containing one or more ether oxygen atoms; $R^{iv}$ is alkylene of 1 to 8 carbon atoms; $R^{ii}$ is hydrogen or alkyl of 1 to 8 carbon atoms in which the carbon chain may be interrupted by one or more ether oxygen atoms, or (c) n is 3, and X is

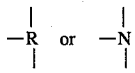

in which R is as defined above but with 3 bond sites with the proviso that the electrochemical fluorination is conducted under the following conditions: current density of about 10 to 600 amps per square meter of anode surface; and a temperature sufficient to maintain a boiling hydrogen fluoride liquid phase during the fluorination.

6. The process of claim 5, wherein n is 1; R is alkyl of 1–8 carbon atoms; $R^i$ is alkyl of 2 to 8 carbon atoms optionally containing an ether oxygen atom, and $R^{ii}$ and $R^{iii}$ are each independently hydrogen or alkyl of 1 to 4 carbon atoms or when taken together with the nitrogen atom form a 5- or 6- membered heterocyclic ring optionally interrupted by a heteroatom selected from nitrogen, oxygen and sulfur.

7. The process of claim 5, wherein n is 2; $R^i$ is an alkylene of 1 to 8 carbon atoms optionally containing an ether oxygen atom; $R^{iv}$ is alkylene of 1 to 4 carbon atoms; and $R^{ii}$ is hydrogen or alkyl of 1 to 4 carbon atoms.

8. The process of claim 6, wherein the compound is dimethyldisulfone.

9. The process of claim 6, wherein the compound is selected from the group consisting of methyl methanesulfonate, butyl methanesulfonate, octyl methanesulfonate, isopropyl methanesulfonate and morpholinomethane sulfonamide.

10. The process of claim 7 wherein the compound is N, N-bis-methane sulfonimide.

11. A method of preparing perfluoroalkanesulfonyl fluorides which comprises using in an electrochemical fluorination process, a compound of the formula $(RSO_2)_nX$ wherein R is alkyl of 1 to 20 carbon atoms in which the carbon chain may be interrupted by one or more ether oxygen atoms;

(a) n is 1, and X is —$R^i$, —$OR^i$, —$NR^{ii}R^{iii}$ or —$SO_2R$, in which R is as defined above; $R^i$ is R; $R^{ii}$ and $R^{iii}$ are each independently hydrogen or alkyl of 1 to 8 carbon atoms in which the carbon chain may be interrupted by one or more ether oxygen atoms, or when taken together with the nitrogen atom form a five to seven membered heterocyclic ring optionally interrupted by a heteroatom selected from nitrogen, oxygen and sulfur; with the proviso of excluding dimethylsulfone and diethylsulfone;

(b) n is 2, and X is —$R^i$—, —$OR^i$—, —$OR^{iv}$O— or

—$NR^{ii}$, in which $R^i$ is an alkylene of 1 to 20 carbon atoms optionally containing one or more ether oxygen atoms; $R^{iv}$ is alkylene of 1 to 8 carbon atoms; $R^{ii}$ is hydrogen or alkyl of 1 to 8 carbon atoms in which the carbon chain may be interrupted by one or more ether oxygen atoms, or (c) n is 3, and X is

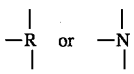

in which R is as defined above but with 3 bond sites with the proviso that the electrochemical fluorination is conducted under the following conditions: current density of about 10 to 600 amps per square meter of anode surface; and a temperature sufficient to maintain a boiling hydrogen fluoride liquid phase during the fluorination.

12. The method of claim 11, wherein R is alkyl of 1–8 carbon atoms in which the carbon chain may be interrupted by one or more ether oxygen atoms.

13. The method of claim 12, wherein n is 1; $R^i$ is R, and $R^{ii}$ and $R^{iii}$ are each independently hydrogen or alkyl of 1 to 4 carbon atoms or when taken together with the nitrogen atom form a 5- or 6- membered heterocyclic ring optionally interrupted by a heteroatom selected from nitrogen, oxygen and sulfur.

14. The method of claim 12, wherein n is 2; $R^i$ is alkylene of 1 to 4 carbon atoms optionally containing an ether oxygen atom, and $R^{ii}$ is hydrogen or alkyl of 1 to 4 carbon atoms.

15. A method of preparing perfluoromethanesulfonyl fluoride which comprises using in an electrochemical fluorination process, a compound of the formula $(CH_3SO_2)_nX$ wherein (a) n is 1, and X is —$R^i$, —$OR^i$, —$NR^{ii}R^{iii}$ or —$SO_2R$, in which R is alkyl of 1 to 20 carbon atoms in which the carbon chain may be interrupted by one or more ether oxygen atoms; $R^i$ is alkyl of 2 to 20 carbon atoms in which the carbon chain may be interrupted by one or more ether oxygen atoms; $R^{ii}$ and $R^{iii}$ are each independently hydrogen or alkyl of 1 to 8 carbon atoms in which the carbon chain may be interrupted by one or more ether oxygen atoms, or when taken together with the nitrogen atom form a five to seven membered heterocyclic ring optionally interrupted by a heteroatom selected from nitrogen, oxygen and sulfur;

(b) n is 2, and X is —$R^i$—, —$OR^i$—, —$OR^{iv}O$— or

—$NR^{ii}$, in which $R^i$ is an alkylene of 1 to 20 carbon atoms optionally containing one or more ether oxygen atoms; $R^{iv}$ is alkylene of 1 to 8 carbon atoms; $R^{ii}$ is hydrogen or alkyl of 1 to 8 carbon atoms in which the carbon chain may be interrupted by one or more ether oxygen atoms, or (c) n is 3, and X is

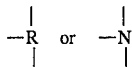

in which R is as defined above but with 3 bond sites with the proviso that the electrochemical fluorination is conducted under the following conditions: current density of about 10 to 600 amps per square meter of anode surface; and a temperature sufficient to maintain a boiling hydrogen fluoride liquid phase during the fluorination.

16. The method of claim 15 wherein n is 1; R is alkyl of 1–8 carbon atoms; $R^i$ is alkyl of 2 to 8 carbon atoms optionally containing an ether oxygen atom, and $R^{ii}$ and $R^{iii}$ are each independently hydrogen or alkyl of 1 to 4 carbon atoms or when taken together with the nitrogen atom form a 5- or 6- membered heterocyclic ring optionally interrupted by a heteroatom selected from nitrogen, oxygen and sulfur.

17. The method of claim 15, wherein n is 2; $R^i$ is an alkylene of 1 to 4 carbon atoms optionally containing an ether oxygen atom; $R^{iv}$ is alkylene of 1 to 4 carbon atoms; and $R^{ii}$ is hydrogen or alkyl of 1 to 4 carbon atoms.

18. The method of claim 16, wherein the compound is dimethyl disulfone.

19. The method of claim 16, wherein the compound is selected from the group consisting of methyl methanesulfonate, butyl methanesulfonate, octyl methanesulfonate, isopropyl methanesulfonate and morpholinomethane sulfonamide.

20. The method of claim 17, wherein the compound is N, N- bis-methane sulfonimide.

* * * * *